United States Patent [19]

Brisson

[11] Patent Number: 5,176,625
[45] Date of Patent: Jan. 5, 1993

[54] STENT FOR URETER

[76] Inventor: A. Glen Brisson, 22358 Timberlea La., Kildeer, Ill. 60047

[21] Appl. No.: 604,088

[22] Filed: Oct. 25, 1990

[51] Int. Cl.5 ............................................. A61M 25/00
[52] U.S. Cl. ..................................... 604/8; 604/281; 604/9; 604/10
[58] Field of Search ...................... 604/8-10, 604/282, 281, 280; 128/776, 687

[56] References Cited

U.S. PATENT DOCUMENTS

| | | | |
|---|---|---|---|
| 4,610,657 | 9/1986 | Densow | 604/8 |
| 4,713,049 | 12/1987 | Carter | 604/8 |
| 4,764,114 | 8/1988 | Jeffcoat et al. | 433/72 |
| 4,790,809 | 12/1988 | Kuntz | 604/8 |
| 4,820,262 | 4/1989 | Finney | 604/8 |
| 4,874,360 | 10/1989 | Goldberg et al. | 604/8 |
| 4,950,228 | 8/1990 | Knapp, Jr. et al. | 604/8 |
| 5,052,998 | 10/1991 | Zimmon | 604/8 |

*Primary Examiner*—Robert A. Hafer
*Assistant Examiner*—Kerry Owens

[57] ABSTRACT

A ureteral stent is nominally straight, but is provided with a coil adjacent one end to prevent migration. The coil portion is straightened upon insertion into the ureter on a guide wire, and is supposed to coil after insertion to prevent migration. An electronic signal is provided when such coiling does take place, and is applied to externally human descernable structure such as a meter. Various embodiments of the invention are disclosed, and may include a metallic cylinder embedded in the end of the stent and disposed adjacent a coil within the straight portion of the stent for inductive relation when the coiled portion has properly coiled following insertion.

14 Claims, 2 Drawing Sheets

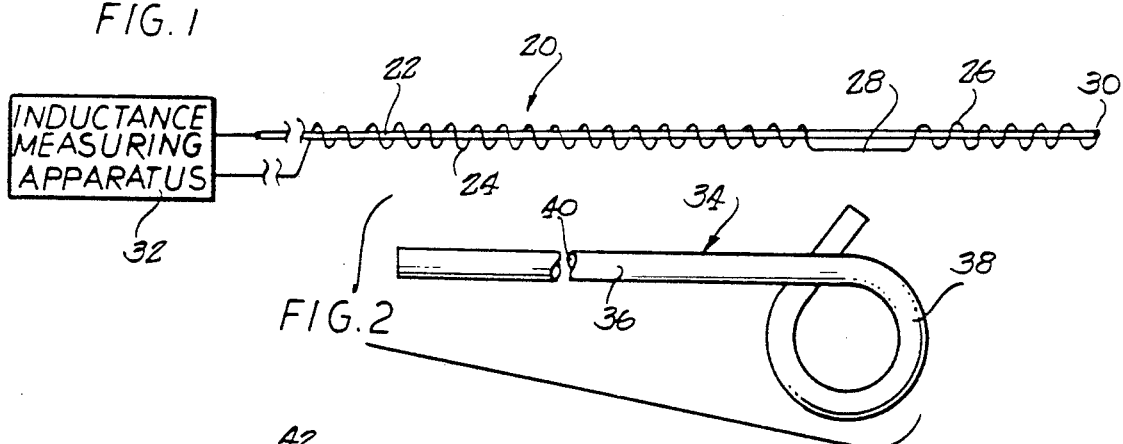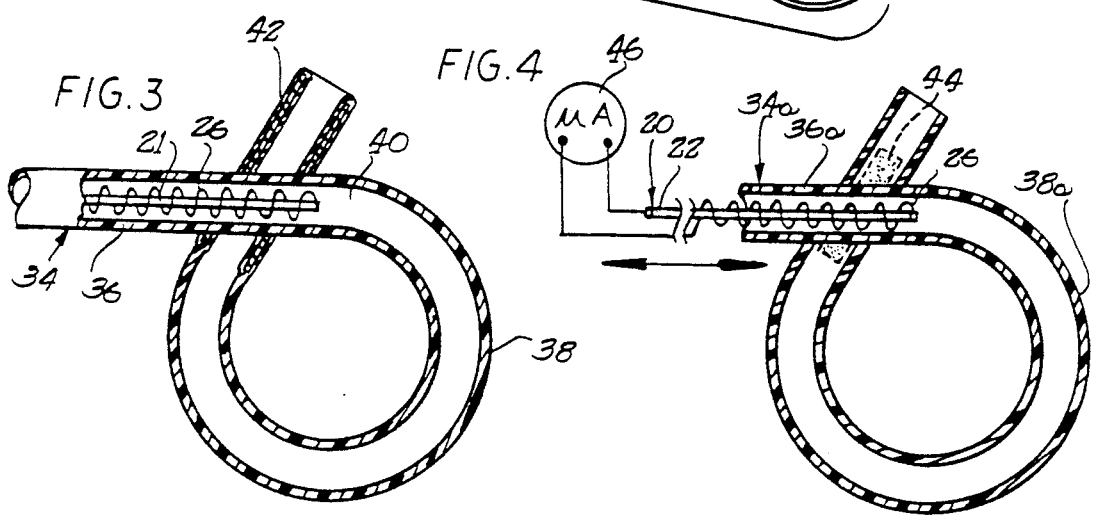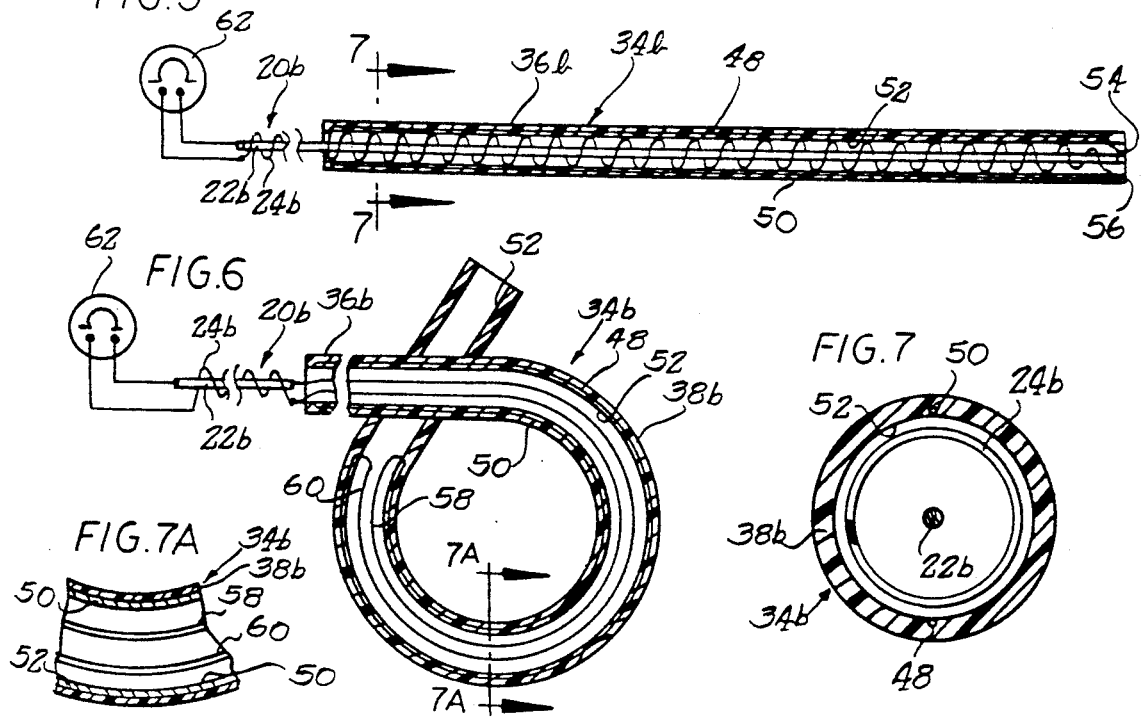

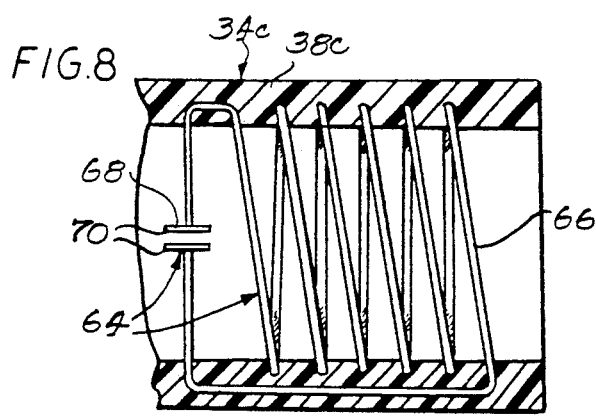
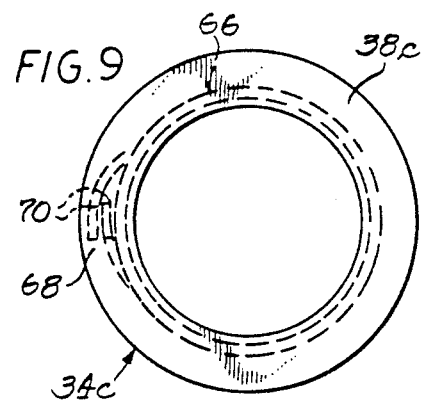
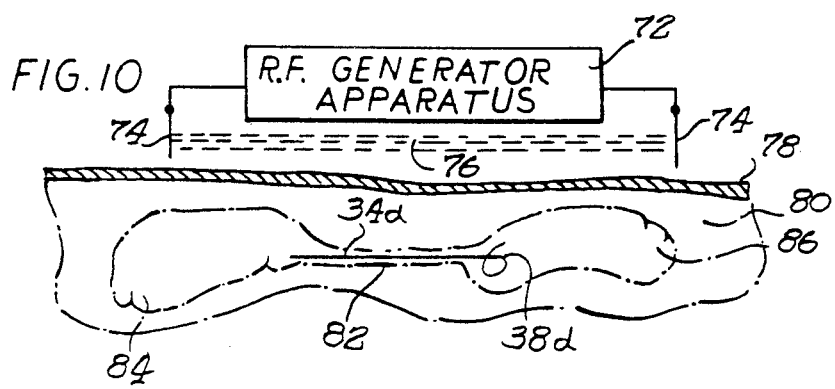
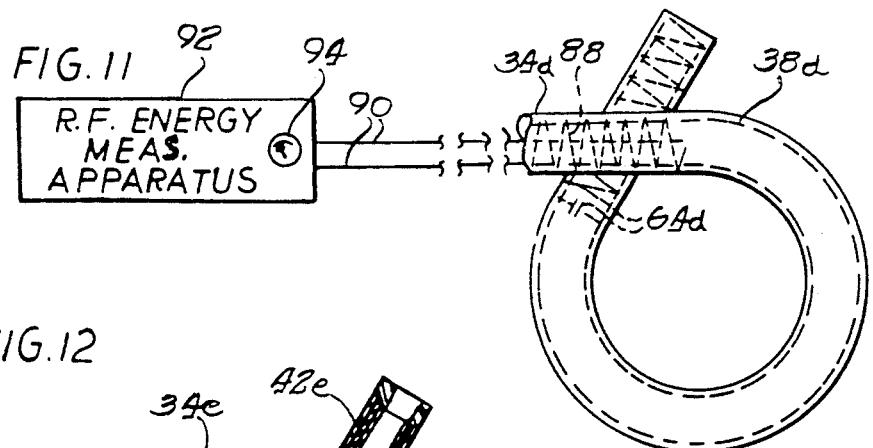
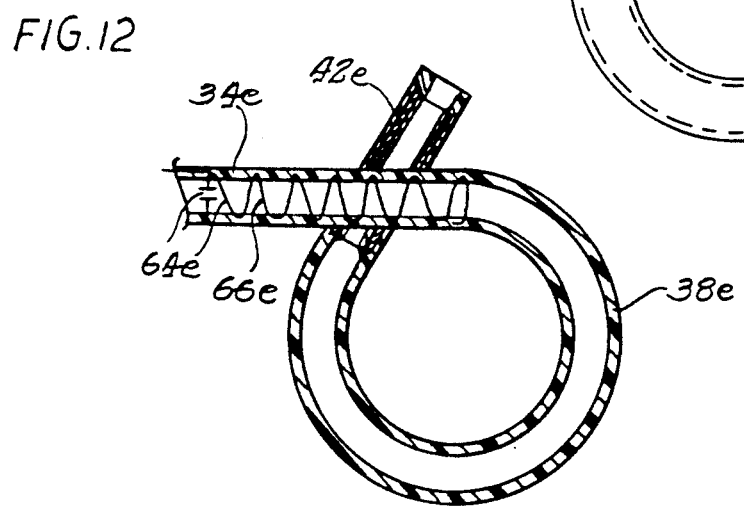

STENT FOR URETER

BACKGROUND OF THE INVENTION

There are various reasons why a ureter may fail totally or in part to carry urine from the kidneys to the bladder. This is a serious medical condition that may be life threatening in its implications. Procedures are known for placing a catheter or stent through the ureter from one end to the other to ensure proper carrying of urine from the kidneys to the bladder. This may be for a short term or for a very long term.

There is a tendency for a ureter catheter or stent to tend to migrate from its position in the catheter, typically from the kidneys to the bladder. This is highly undesireable, and may totally defeat the purpose of the stent. Efforts have been made to prevent such migration, and typically comprise coiling of one or both ends of the stent. A stent is inserted by a quasi-surgical procedure lengthwise from the bladder into the kidneys, and the stent must be straight for this purpose. Accordingly, a stent, which typically is made of silicone is preconditioned to a curve, but it is straightened by an inserting wire or the like. It is often very difficult to tell if the stent end has properly coiled into its premolded position after insertion and after removal of the inserting wire.

OBJECTS AND SUMMARY OF THE PRESENT INVENTION

It is an object of the present invention to provide superior means for assertaining whether a stent end has properly coiled following insertion and removal of the inserting wire.

More particularly, it is an object of the present invention to provide electronic means for assertaining whether the end of a stent has properly coiled following insertion.

In accordance with the present invention a ureteral stent is provided at one end (or at both ends) with electronic elements which cooperate with one another when the stent end is coiled, but which do not cooperate when the stent end remains straight or not properly coiled. Electronic measures can be utilized to determine the extent of cooperation, if any, of the electronic elements, and thereby to determine whether the stent end has properly coiled.

In the various embodiments of the invention as herein after set forth, illustration is made of only one end of the stent coiling. This can be either end, either at the kidney or at the bladder, and it is certainly within the province of the present invention to have both ends of the stent coiled, i.e. both in the kidney and in the bladder.

THE DRAWINGS

The present invention will best be understood when taken in conjunction with the accompanying drawings wherein:

FIG. 1 is an electrical, generally schematic view illustrating the principles of the present invention;

FIG. 2 is a side view of a properly coiled stent corresponding to the illustrated in FIG. 1;

FIG. 3 is a longitudinal section through the end portion of the stent corresponding to the end portion of FIG. 2 and showing the structure thereof;

FIG. 4 is a view generally similar to FIG. 3 and showing the further modification of the invention;

FIG. 5 is a longitudinal sectional view of a stent embodying a further modification of the invention;

FIG. 6 is a view of the end portion of the stent, generally similar to FIG. 3. but embodying the invention of FIG. 5;

FIG. 7 is a cross-sectional view on an enlarged scale taken substantially along the line 7—7 in FIG. 5;

FIG. 7A is a further enlarged detailed sectional view along the line 7A—7A in FIG. 6;

FIG. 8 is longitudinal sectional view of an end portion of the stent embodying yet another form of the present invention;

FIG. 9 is a view taken from the right end of FIG. 8;

FIG. 10 is a somewhat schematic view of a human body in section, showing the kidney and bladder with a stent extending there between, and with an external radio frequency field established over the surface of the body for a further embodiment of the invention;

FIG. 11 is a view generally similar to FIG. 3 of the coiled end of the coiled end of the stent in accordance with the form of the invention illustrated in FIG. 10;

FIG. 12 is a view generally similar to FIG. 3 of a coiled end of a stent illustrating yet another embodiment of the invention.

DETAILED DISCLOSURE OF THE ILLUSTRATED EMBODIMENTS

The first embodiment of the present invention is illustrated in FIGS. 1-3, and attention first should be directed to FIG. 1. The guidewire for the insertion of a stent is shown at 20, and comprises two parts. There is an inner part 22 which generally comprises a stainless steel wire which for purposes of the present invention may be considered straight. However, this wire must be sufficiently flexible to conform to body contours when inserted through the ureter. In addition, there is an outer wire 24 which is helically wound of bare wire and of a suitable diameter which allows it to slide over the solid inner wire. The inner wire is insulated with a suitable plastic coating such as Teflon plastic material. The outer wire 24 is wound into a helix as a bare wire, and subsequently is dipped in or otherwise coated with Teflon. As a result, the windings of the outer wire are not electrically insulated from each other. Therefore, the outer wire forms a continuous electrical shield over the inner wire. As a result, the two piece guidewire 20 essentially comprises a two conductor cable. The inner wire 22 extends axially considerably beyond the outer wire 24. A coil 26 of very fine insulated wire (such as enameled magnet wire) is electrically connected to the outer wire 24 and 28, and extends to the end of the inner wire 22 to which it is electrically connected at 30. The thin helically coiled wire 26 may be essentially free form, or it may be wound on a nonmetallic extension of the outer wire 24.

The inner and outer wires 22 and 24 are connected to an inductance-measuring apparatus 32. Such apparatuses are known in the art, and need not be further discussed here.

A ureteral stent 34 will be seen in FIG. 2, and comprises a straight portion 36 and a coiled end portion 38. This coiling is affected during formation of the stent, which is in the form of a tube, generally made out of silicone rubber. The stent 34 is axially hollow as indicated at 40. The stent is of generally conventional construction, but in FIG. 3 it will be seen that a cylinder 42 of a suitable metal, preferably ferric, is molded in the tip portion of the stent, particularly at the extremity of the coiled portion 38. As will be understood, the stent is straightened by being extending on and slid over the insertion wire 20. It is pushed beyond the end of the wire, and if all goes well, the stent will coil as indicated at 38. As will be seen in FIG. 3, this places the metallic cylinder 42 in close proximity to the winding 26. Disposition of the metallic cylinder 42 adjacent the wire 26 materially changes the inductance of the wire, as will be understood. This change in inductance is readily measured by the inductance-measuring apparatus 32, and it is possible to tell if a perfect coiling is obtained or if the coil is at least sufficient to prevent inadvertent axial migration of the stent. If there is no change in inductance from the straightened, insertion possible, it will be known that something has interferred with the coiling of the stent, and that it is necessary to do something about this, or to expect migration of the stent.

A modification of the invention is shown in FIG. 4. The guidewire 20 remains as before end, the same numbers are used. However, the stent is somewhat modified, and hence similar numerals are used with the addition of the suffix a. The distinction is that rather than having a metallic cylinder 42 in the end of the stent, there is a magnet 44 embedded in the wall of the stent. The magnet may be simply a bar magnet or it may be cylindrical. The electrical leads from the center wire 22 and from the wire 26 are connected to the voltage or current sensing device, such as a microammeter 46. After the stent has been installed, and the guidewire 20 partially withdrawn so that the stent may coil as indicated at 38A, the wire 20, and hence the coil 26 are moved axially back and forth. Movement of the coil 26 past the magnet 44 generates electricity, and the current generated is measured by the microammeter 46. Other means of detecting the electricity generated include earphones, perhaps with amplification.

A further embodiment of the invention is shown in FIGS. 5-7A. In this embodiment of the invention, an electrical connection is made to the stent itself. Specifically, a variable resistance stress sensing wire is molded into the stent, and this wire is then connected to a resistance measuring device located outside of the body.

More specifically, the insertion wire 20b, similar numerals being used in this embodiment with the addition of the suffix b to identify similar parts, includes a central wire 22b and an encircling coil 24b, again insulated after being formed into a coil. In the present instance the stent is also somewhat altered, and includes in particular stress wires 48 and 50 are molded into the side wall 54 of the stent. The wires are connected at their extremities 54 and 56 to the center wire 22b and coil 24b of the insertion wire 20b. As the insertion wire 20b is partially withdrawn to allow the end of the stent to form into a curl or loop as shown in FIG. 6 portions of the wires 48 and 50 are stripped from the wall and simply extend through the stent as shown at 58 and 60. Stress wires are known in the art, and have a different resistance when they are curved and when they are straight. Thus, the resistance of the wires will indicate if the stent end has properly curled into the loop as shown in FIG. 6. After this has been determined, the insertion wire 20b can be pulled entirely away from the stent, thus totally stripping out the wires 48 and 50 for removal thereof from the body.

Various means can be used for measuring the change in resistance when the wires 48 and 50 are coiled from their previous straight condition, and an ohmmeter 62 is shown in FIGS. 5 and 6 connected to the center wire 22b and the coil 24b for measuring this resistance change.

A further embodiment of the invention is shown in FIG. 8. The structure in this case is substantially the same as in the embodiment in FIGS. 1-3, except that the end portion 36c of the stent 34c has a resonant circuit 64 molded into the end portion 38c. The resonant circuit includes a coil 66 and a capacitor 68 having plates 70, all of which are molded in the wall of the stent and protected by the rubber construction thereof. Instead of the inductance measuring apparatus of FIG. 1, there would be a radio frequency generating apparatus including a meter showing the power dispersed attached to the two wires about the insertion wire. Radio frequency would be broadcast into the air from the coil 26 of the insertion wire, but only after the insertion wire had been partially withdrawn so as not to be in proximity to the resonant circuit 64. If the end portion 36c of the stent properly coiled as intended following such withdrawal, then the resonant circuit would be adjacent the coil 26. Radio frequency power would be induced into the coil 66 of the resonant circuit, and more power therefore would be taken from the radio frequency generator, and the physician would then be sure that the end of the stent had properly curved into the coiled position.

Yet another embodiment of the invention is shown in FIGS. 10 and 11. In this instance there is a radio frequency generator apparatus 72 connected to antennas 74 to establish a radio frequency field 76 adjacent to the epidermis 78 of the body 80 of a patient. The internal portions of the body including the ureter 82, the bladder 84, and a kidney 86 are shown rather generally, with a stent 34d extending from the bladder into the kidney, and having a coiled end portion 38d within the kidney.

The stent has a resonant circuit 68d essentially identical with that previously disclosed in connection with the embodiment in FIGS. 8 and 9. In addition, it has an antenna coil 88 connected by wires 90 extending from the body and to a radio frequency energy means 92 including a meter 94.

The antennae coil 88 will receive radio frequency energy from the field 76. If the end 38d of the stent 34d properly coils as intended, then the resonant circuit 64d will be in inductive relation with the antennae coil 88, and therefore will absorb energy therefrom. The meter 94 shows how much energy is being taken from the energy means or generator 72 so that it can be assertained if the end of the stent has properly coiled as intended.

A final embodiment of the invention is illustrated in FIG. 12. In this embodiment the guide wire or insertion wire is not used for carrying a signal, and can be a conventional guidewire. An external radio frequency field is developed over the surface of the body in the vicinity of the kidney, ureter, and bladder. A metallic, preferably ferric, cylinder 42e is molded in the end of the stent adjacent the coiled portion 38e. A resonant circuit 64e is molded in the straight portion of the stent adjacent where the coil should take place. When the coil is complete, the metallic sleeve 42e will be proximate to the coil 66e of the resonant circuit, thereby changing the resonant frequency. The radio frequency field is at the frequency to which the circuit should be resonant with the sleeve 42e in position as shown in FIG. 12, and thus more energy is absorbed from the radio frequency field with a properly formed coil. This readily can be measured by a meter in the radio frequency energy means apparatus or generator by measuring the amount of radio frequency energy dispensed.

It will now be apparent that there have been disclosed several different structures for electronically assertaining whether the end of a stent has properly coiled following insertion and removal or partial removal of the guide or insertion wire. In each case concern has been with the entry end of the stent, and this would be in the kidney. However, the structures apply equally well to the bladder end of the stent and it is apparent that the stent could coil at both ends and be checked by the structures shown.

The specific examples of the invention as herein shown and described are for illustrative purposes only. Various changes in structure will no doubt occur to those skilled in the art, and will be understood as forming a part of the present invention in so far as they fall within the spirit and scope of the appended claims.

The invention is claimed as follows:

1. The combination for electrically determining if the end of a ureteral stent has properly coiled after insertion comprising a stent having a nominally coiled distal end portion and a nominally straight portion, said nominally straight portion when installed extending through a ureter fron end-to-end thereof and said nominally coiled distal end portion extending beyond said ureter, electronic sensing means disposed in said nominally straight portion of said stent and in said nominally coiled distal end portion of said stent, said electronic sensing means with said distal end portion coiled overlapping itself and thereby providing a different electronic indication when said nominally coiled distal end portion is properly coiled than when it is not properly coiled, and humanly discernable means operated by said sensing means and providing humanly discernable criteria of said electronic indication.

2. The combination as set forth in claim 1 wherein said electronic sensing means includes a metallic cylinder embedded in the nominally coiled distal end portion of said stent.

3. The combination as set forth in claim 1 wherein said sensing means includes a magnet disposed in the nominally coiled distal end portion of said stent for coaction with said sensing means in said nominally straight portion.

4. The combination as set forth in claim 2, wherein said sensing means includes a coil disposed in the nominally straight portion of said stent and in inductive relation with said metallic cylinder when said nominally coiled distal end portion has properly coiled.

5. The combination as set forth in claim 3 wherein said sensing means comprises a coil disposed in the nominally straight portion of said stent and in inductive relation with said magnet when said nominally coiled distal end portion has properly coiled following insertion.

6. The combination as set forth in claim 1 and further including a guide wire over which said stent is inserted into a ureter, and wherein said guide wire comprises a portion of said electronic sensing means.

7. The combination as set forth in claim 6 and further including a coil electrically connected to said guidewire and comprising a portion of said sensing means, and disposed for inductive cooperation with the nominally coiled distal end portion of said stent following proper coiling thereof.

8. The combination as set forth in claim 7 and further including a magnet disposed in the nominally coiled portion of said stent for inductive relation with said coil.

9. The combination as set forth in claim 1 wherein said sensing means comprises a stresswire extending through at least a portion of said nominally straight portion of said stent and into the coiled portion of said stent, and having a different resistance when coiled than when said nominally coiled portion is straightened upon insertion.

10. The combination as set forth in claim 1 wherein said sensing means includes a resonant circuit in said nominally coiled distal end portion, and means establishing a radio frequency field at a resonant frequency, greater radio frequency energy being absorbed by said resonant circuit when said nominally coiled distal end portion if properly coiled.

11. The combination as set forth in claim 10 wherein said stent has a side wall of elastomeric material, and said resonant circuit comprises a coil and a capacitor embedded within said side wall adjacent the nominally coiled distal end portion thereof.

12. The combination as set forth in claim 10 and further including a wire extending substantially through said stent to provide radio frequency energy to said resonant circuit.

13. The combination as set forth in claim 10 and furder including means for generating a radio frequency field external to but adjacent to the epidermis of the body in which the stent is installed, a greater amount of radio frequency energy being absorbed by said resonant circuit when said nominally coiled portion is properly coiled.

14. The combination as set forth in claim 13 wherein said resonant circuit comprises a coil and a capacitor in said nominally straight portion of said stent adjacent said nominally coiled portion, and a metallic cylinder in said nominally coiled distal end portion of said stent, there being a change in resonant frequency and the amount of radio frequency energy absorbed when said nominally coiled distal end portion is properly coiled to bring said metallic cylinder into proximity to said coil.

* * * * *